United States Patent [19]

Sarantakis

[11] Patent Number: 5,185,340
[45] Date of Patent: Feb. 9, 1993

[54] PYRIMIDINYL ARYLALKYL ETHERS WITH ANTIHYPERTENSIVE ACTIVITY

[75] Inventor: Dimitrios Sarantakis, Newtown, Pa.

[73] Assignee: American Home Products Corporation, New York, N.Y.

[21] Appl. No.: 925,713

[22] Filed: Aug. 4, 1992

[51] Int. Cl.$^5$ .................. C07D 239/34; A61K 31/505
[52] U.S. Cl. .................................... 514/269; 514/258; 544/319; 544/253
[58] Field of Search ................ 514/269, 258; 544/319, 544/253

[56] References Cited

U.S. PATENT DOCUMENTS 5,100,897 3/1992 Allen et al. .................. 514/269

Primary Examiner—John M. Ford
Attorney, Agent, or Firm—R. F. Boswell, Jr.

[57] ABSTRACT

The compounds of this invention having Angiotensin II receptor binding properties and thus useful in the treatment of hypertension are of the formula:

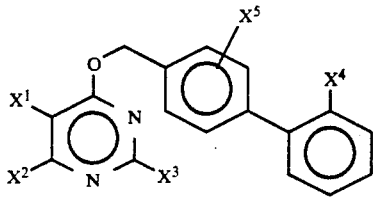

wherein:
$X^1$ = H, lower alkyl, phenyl or naphthyl;
$X^2$ is $X^1$, perfluoroalkyl or halogen;
$X^1$ and $X^2$ together are —$(CH_2)_n$— where n is 3-6;
$X^3$ = H, lower alkyl, perfluoroalkyl, perchloroalkyl or halogen;
$X^4$ = 5-tetrazolyl, carboxy or cyano;
$X^5$ = H, lower alkoxy or halogen;

and the pharmaceutically acceptable salts thereof.

11 Claims, No Drawings

PYRIMIDINYL ARYLALKYL ETHERS WITH ANTIHYPERTENSIVE ACTIVITY

FIELD OF INVENTION

This invention relates to novel pyrimidinyl arylalkyl ethers and their use in the treatment of hypertension through their competitive binding with angiotensin II receptors. Drugs which interfere with the renin-angiotensin system by inhibition of renin, an enzyme that converts angiotensinogen to angiotensin I, or inhibition of angiotensin converting enzyme (ACE inhibitor) which converts angiotensin I to the vasoactive angiotensin II, or which bind competitively at the angiotensin II receptor site as do the compounds of this invention can be useful in the treatment of hypertension.

BACKGROUND OF THE INVENTION

4-Biphenylmethoxypyridines or 4-benzyloxypyridines having angiotension antagonist properties and thus useful for the treatment of hypertension, congestive heart failure, hyperaldosteronism and renin angiotensin-aldosterone disorders are disclosed in the European patent application EP 453210A. 4-Biphenylmethoxyquinolines and 4-benzyloxyquinolines having the same activity as the pyridine analogs are disclosed in the European Patent Application EP 456,442A. Biphenyl-substituted pyrimidinones used as angiotensin II antagonists in the treatment of hypertension, hyperaldosteronism, renal failure, etc., are disclosed in the European Patent Application EP 419048A.

DESCRIPTION OF THE INVENTION

The novel compounds useful in the method of this invention have the structure shown below as Formula I:

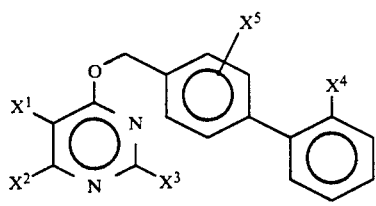

wherein:
$X^1$ = H, lower alkyl, phenyl or naphthyl;
$X^2$ = H, lower alkyl, phenyl, naphthyl, perfluoroalkyl or halogen;
or
$X^1$ and $X^2$ together are $-(CH_2)_n-$ where n is 3-6;
$X^3$ = H, lower alkyl, perfluoroalkyl, perchloroalkyl or halogen;
$X^4$ = 5-tetrazolyl, carboxy or cyano;
$X^5$ = H, lower alkoxy or halogen;
and the pharmaceutically acceptable salts thereof.

In a more preferred aspect of this invention, the groups $X^1-X^5$ of the Formula I compound have the following definitions:
$X^1$ = H, $-CH_3$, $-CH_2CH_2CH_3$, $-CH(CH_3)_2$, $-C(CH_3)_3$, phenyl or naphthyl;
$X^2$ = H, $-CH_3$, $-CH_2CH_3$, $-CH_2CH_2CH_3$, $-CH(CH_3)_2$, $-C(CH_3)_3$, phenyl, napthyl, $-CF_3$, $-CF_2CF_3$, Cl, Br or F;
or
$X^1$ and $X^2$ together are $-(CH_2)_3-$ or $-(CH_2)_4-$
$X^3$ = trifluoromethyl or methyl
$X^4$ = 5-tetrazolyl,
and
$X^5$ = H, $-OCH_3$, F, Cl or Br.

In a further definition of groups $X^1-X^5$ under Formula I, lower alkyl is $C_1-C_6$ alkyl, lower alkoxy is $-O-$lower alkyl, perfluoroalkyl is lower alkyl where all hydrogen atoms are replaced with fluorine atoms, perchloroalkyl is lower alkyl where all hydrogen atoms are replaced with chlorine atoms, and halogen means fluorine, chlorine or bromine.

The compounds of this invention may also form solvates and/or salts with inorganic or organic bases. Any pharmaceutically acceptable salts of these compounds are within the scope of this invention. These salts may be, but are not limited to, ammonium salts, alkali metal salts such as sodium and potassium, alkaline earth metal salts such as calcium, dicyclohexylamine salts, TRIS salts, and salts of amino acids. These compounds may also be converted to N-oxides by treatment with hydrogen peroxide by conventional means.

The preferred compounds of this invention are most readily prepared by reacting the sodium salt of an appropriately substituted 4-pyrimidinol, formed by treatment of the 4-pyrimidinol with sodium methoxide, with 5-(4'-bromomethylbiphenyl-2-yl)-1-trityl-1H-tetrazole in an aprotic solvent such as dimethylformamide to obtain the trityl protected ether. The trityl protecting group on the tetrazole group of the ether is then removed by treatment with acid such as methanolic HCl, acetic acid or trifluoroacetic acid to obtain the final product. The reaction sequence is summarized in the following reaction sequence:

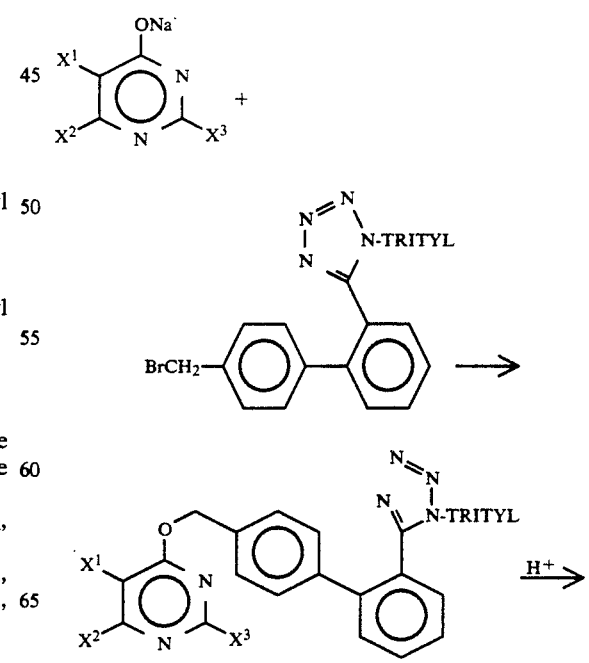

-continued

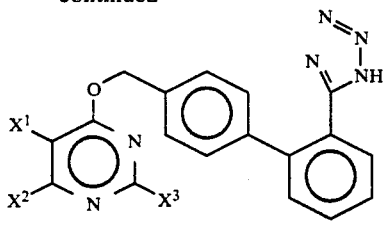

The following specific examples are for illustrative purposes only and should not be construed as limiting this disclosure which is limited only by the scope of the appended claims.

EXAMPLE 1

4-Hydroxy-6-ethyl-5-propyl-2-(trifluoromethyl)pyrimidine.

A mixture of ethyl 2-n-propylacetoacetate (0.5 mole), trifluoroacetamidine (0.67 mole) and sodium ethoxide (1 mole) in ethanol was heated at reflux temperature overnight and then evaporated to dryness. The residue was triturated in water and acidified with glacial acetic acid to yield the title compound. TLC, Silica gel (cyclohexane-ethyl acetate, 1:1) $R_f 0.80$ $^1$H NMR (CDCl$_3$): δ 0.95 (t,3H) 1.25 (t,3H) 1.57 (m,2H) 2.58 (q,2H) 2.70 (q,2H).

EXAMPLE 2

4-Hydroxy-2-trifluoromethyl-5,6,7,8-tetrahydroquinazoline.

A mixture of ethyl 2-cyclohexamonecarboxylate (85 g, 0.5 mole), trifluoroacetamide (50 ml, 0.67 mole) and sodium ethoxide (68 g, 1.0 mole) in ethanol was heated at reflux temperature overnight and then evaporated to dryness. The residue was triturated with water and acidified with glacial acetic acid to obtain 86 g of product as a white solid. TLC, Silica. gel. (cyclohexane-ethyl acetate, 1:1) $R_f 0.55$ $^1$H NMR (CDCl$_3$): δ 1.80 (m,4H) 2.60 (t,2H) 2.75 (t,2H)

EXAMPLE 3

4-Hydroxy-2,5-dimethyl-6-(trifluoromethyl)pyrimidine.

Ethyl 3-keto-2-methyl-4,4,4-trifluorobutyrate (40 g, 0.2 mole) was added to a mixture of sodium methoxide (32.4 g) and acetamidine hydrochloride (20 g) in methanol. The mixture was refluxed overnight and then evaporated to dryness. The residue was partitioned between aqueous acetic acid and ethyl acetate. The organic layer was washed twice with water and dried over magnesium sulfate. Evaporation of the solvent provided 35 g of crystalline solid. TLC, Silica gel. (chloroform-methanol, 10:1) $R_f 0.60$. (cyclohexane-ethyl acetate, 1:1) $R_f 0.25$ $^1$H NMR (CDCl$_3$): δ 2.21 (d,3H) 2.53 (s,3H).

EXAMPLE 4

6-Ethyl-5-propyl-4-[[2'-(1H-tetrazol-5-yl)[1,1'-biphenyl]-4-yl] methoxy]-2-(trifluoromethyl)pyrimidine.

4-Hydroxy-6-ethyl-5-propyl-2-(trifluoromethyl)-pyrimidine (1.2 g, 5 mmole) was converted to the sodium salt with sodium methoxide (275 mg). The sodium salt was dissolved in DMF and mixed with 2.8 g (5 mmole) of 5-(4'-bromomethylbiphenyl-2-yl)-1-trityl-1H-tetrazole [U.S. Pat. No. 4,870,186], and the mixture heated at 50° C. for 18 hours. The solvent was evaporated to dryness and the residue was triturated with excess water to give a gum which was extracted into EtOAc. The organic layer was washed with H$_2$O twice, dried over Na$_2$SO$_4$ and evaporated to a thick oil (4 g). One gram of this oil was treated with dry HCl saturated methanol for 3 hours then evaporated to dryness. The residue was triturated with hexane twice and decanted to afford a gum. The rest of the material was treated in the same way to provide a total of 2 g of crude product. Flash chromatography through silica gel and elution with CHCl$_3$ contg. 4% MeOH gave 210 mg of the desired compound as a white solid. TLC, Silica gel (CHCl$_3$-MeOH-NH$_4$OH,7:3:2%) $R_f 0.55$ MS (DCI) [M+H]$^+$469

Analysis Calcd. for C$_{24}$H$_{23}$N$_6$F$_3$O: C, 61.53; H, 4.95; N 17.94. Found: C, 62.13; H, 5.05; N 18.06. $^1$H NMR (DMSO-d$_6$): δ 0.91 (t,3H) 1.20 (t,3H) 1.50 (q,2H) 2.21 (q,2H) 2.80 (q,2H) 5.43 (s,2H) 7.12 (d,2H) 7.41 (d,2H) 7.50–7.80 (m,4H).

EXAMPLE 5

4-[[2'-(1H-Tetrazol-5-yl)-biphenyl-4-yl]methoxy]-2-trifluoromethyl-5,6,7,8-tetrahydroquinazoline.

Following the procedure of Example 4 and substituting 4-hydroxy-2-trifluoromethyl-5,6,7,8-tetrahydroquinozoline (1.1 g, 5 mmol) for 4-hydroxy-6-ethyl-5-propyl-2-(trifluoromethyl)pyrimidine, 300 mg of the title compound is obtained after flash chromatography of the crude product using 5% methanol in chloroform as the eluting solvent. The monosodium salt dihydrate was obtained after careful titration with 1N sodium hydroxide solution. TLC, Silica gel. (CHCl$_3$-MeOH-NH$_4$OH,7:3:2%) $R_f 0.75$ MS (FAB) [M+H]$^{30}$ 475 [M+Na]$^+$497 $^1$H NMR (DMSO-d$_6$): δ 1.79 (m,4H) 2.60 (t,2H) 2.78 (t,2H) 5.42 (s,2H) 7.15–7.60 (m,8H).

EXAMPLE 6

2,5-Dimethyl-4-[[2'-(1H-tetrazol-5-yl)-biphenyl-4-yl]methoxy]-6-trifluoromethylpyrimidine.

Following the procedure of Example 4 and substituting 4-hydroxy-2,5-dimethyl-6-(trifluoromethyl)pyrimidine (1.1 g, 5 mmol) for 4-hydroxy-6-ethyl-5-propyl-2-(trifluoromethyl)pyrimidine, 400 mg of monohydrate of the title compound was obtained as a white solid after flash chromatography of the crude product (3 g) using 5% methanol in chloroform as the eluting solvent. TLC, Silica gel (CHCl$_3$-MeOH-NH$_4$OH,7:3:2%) $R_f 0.70$ Analysis Calcd. for C$_{21}$H$_{17}$N$_6$F$_3$O.H$_2$O: C, 56.75; H, 4.27; N, 18.91.

Found: C, 56.57H, 3.97N, 18.58 $^1$H NMR (DMSO-d$_6$): δ 2.15 (s,3H) 2.41 (s,3H) 5.25 (s,2H) 7.05–7.20 (q,4H) 7.50–7.70 (m,4H).

The compounds of this invention are useful in treating hypertension as evidenced by in vivo and in vitro laboratory tests as described below.

In Vitro

The high affinity of the compounds for the angiotensin II receptor was established using a rat adrenal receptor binding assay, measuring the displacement of radiolabeled angiotensin II (A II) from the receptor, described as follows: Anesthetize male Sprague-Dawley rats (300–400 g body weight) with CO$_2$ and sacrifice by cervical dislocation. Dissect adrenal glands and keep in ice-cold sucrose buffer. (0.2M sucrose, 1 mM EDTA, 10 mM Trizma base, pH=7.2). Remove medulla by squashing. Mince the cortex, rinse and homogenize in a chilled ground glass tissue grinder with 15 ml sucrose buffer. Centrifuge at 3000× g for 10 min. (Sorvall RCSC centrifuge, SS34 rotor 6200 rpm). Decant supernatant through gauze. Centrifuge combined supernatants at 12000× g for 13 min. (Beckman ultracentrifuge, 80Ti rotor, 13000 rpm). Centrifuge the supernatant from the previous step at 102000× g for 60 min. (Beckman ultracentrifuge, 80Ti rotor, 38200 rpm). All steps are carried out at 4° C. Resuspend the pellet in 0.5 mL assay buffer (50 mM Tris HCl, 5 mM $MgCl_2$, 0.2% BSA (proteasefree), pH=7.4, 25° C.). Store on ice. Determine membrane protein by Lowry or Bradford assay with BSA as standard. The binding assay is performed in triplicate, in 12×75 mm plastic test tubes or in 96-well plate (final volume of 0.25 mL). Add 140 μL assay buffer. Add 10 μL cold A II (to give final concentrations of $10^{-10}-10^{-7}$M for standard curve and $10^{-4}$M for nonspecific binding), compounds (e.g., for final concentrations of 25 and 100 μM, 10 nM and 100 nM) in 50% DMSO, or 50% DMSO as a control. Add 50 μL membrane suspension (e.g., 10 μg protein). Preincubate for 30 min at 25° C. Add 50 μl $^{125}$I-A II which has been prepared as shown below (final concentration = 1 nM). Incubate for 35 min at 25° C. Stop the incubation by adding 1 mL ice-cold buffer (assay buffer without BSA). Filter with GF/C filters on cell harvester (filters are presoaked in the assay buffer containing 1% polyethyleneimine). Rinse assay tubes 3× with 5 mL cold buffer (assay buffer without BSA). Cut and deposit the filter discs into test tubes and count on gamma counter for 1 min. Adjust the specific activity of $^{125}$I-A II purchased from New England Nuclear to 500 μCi/nmole by adding cold A II in water. Calculate the quantities of hot A II and the cold A II needed and make the dilution. Aliquot, seal tight, and store frozen until needed. Calculate the concentration of the total A II (hot+cold) after dilution. On the day of assay, thaw the frozen aliquot and adjust the volume to give a concentration of 5 pmole/mL (or 0.25 pmole/50 μL) with assay buffer (+protease-free BSA). For final concentration of 1 nM$^{125}$I-A II in the assay, add 50 μL (or 0.25 pmole) per test tube to a final volume of 250 μL. The results of these binding assays are reported as the inhibitory concentration of the test compound necessary to achieve fifty percent displacement of radiolabeled angiotensin II from its receptor ($IC_{50}$), or the percent displacement of binding of A II at its receptor at $10^{-8}$M concentration of test compound (% I). All the examples cited in this invention displayed significant inhibition of A II binding in this assay. Typically these compounds displayed an $IC_{50}$ in this assay of less than or equal to 50 μM.

In Vivo

In accordance with their ability to antagonize angiotensin II, the compounds of this invention show antihypertensive action in the following A II-infused rat model. Rats are anesthetized with Dial-Urethane (0.60 mL/kg, ip) and the trachea cannulated with PE 240. Either one femoral artery and both femoral veins or the carotid artery and the corresponding jugular vein are cannulated with PE 50. If the jugular vein is cannulated, two cannulas are placed in the one vein. The initial portion of the duodenum (just distal to the stomach) is cannulated with PE 50 via a small midline incision. Arterial pressure and heart rate are measured from the arterial cannula. Ten to 15 min are allowed following surgery for stabilization of arterial pressure. Ganglion blockade is then produced by intravenous administration of mecamylamine at 3 mg/kg (1 mL/kg of a 3 mg/mL solution). Ganglion blockade causes a fall in arterial pressure of about 50 mmHg. Mecamylamine is given every 90 min throughout the remainder of the experiment. An A II infusion is then begun into the other venous cannula at 0.25 μg/kg/min (at 9.6 uVmin). The A II infusion returns arterial pressure to or slightly above the control level. Once arterial pressure has stabilized with the A II infusion, baseline values for mean arterial pressure (MAP) and heart rate are taken. The test compound, suspended in methyl cellulose, is then administered via the duodenal cannula at 0.1, 3 or, 30 mg/kg in a volume of 1 mL/kg. Mean arterial pressure and heart rate values are tabulated at 15, 30, 60, 90, 120, 150, 180, 210, and 240 min after administration of the test compound.

As illustrated below the compounds of this invention are effective A II antagonists and therefore are useful for treating hypertension. They may also be of value in the prevention of restenosis in the cardiac arteries following balloon angioplasty, the management of acute and chronic congestive heart failure, primary and secondary pulmonary hyperaldosteronism, secondary hyperaldosteronism, primary and secondary pulmonary hypertension, hypertension associated with oral contraceptive use, vascular disorders such as migraine, Raynaud's disease, luminal hyperplasia and the atherosclerotic process, renal diseases or renal complications of other diseases or therapies such as proteinuria, glomerulonephritis, glomerular sclerosis, scleroderma, diabetic nephropathy, end stage renal disease, renal transplant therapy and others. These compounds will also be useful in the treatment of left ventricular dysfunction, diabetic retinopathy, Alzheimers disease, in the enhancement of cognition, in treatment of elevated intraoccular pressure, and in the enhancement of retinal blood flow. The application of the compounds of this invention for these and similar disorders will be apparent to those skilled in the art.

| Biological Activity | |
|---|---|
| Inhibition of 1251-Angiotensin II binding | |
| Example | $IC_{50}$ (nM) |
| 4 | 200 (nM) |
| 5 | 38 nM |

| Reduction of blood pressure in Angiotensin II infused rat | | | |
|---|---|---|---|
| Example | Dose | Time (min) | % decrease in MAP |
| 5 | 3 mg/kg/ml | 15 | 22 |
| | | 90 | 15 |
| | | 240 | 0 |

Pharmaceutical Composition

The antihypertensive compounds of this invention may be administered neat or with a pharmaceutical carrier to a mammal in need thereof. The pharmaceutical carrier may be solid or liquid and the active compound shall be a therapeutically effective amount.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. The dosage to be used in the treatment must be subjectively determined by the attending physician.

What is claimed is:

1. A compound according to the formula:

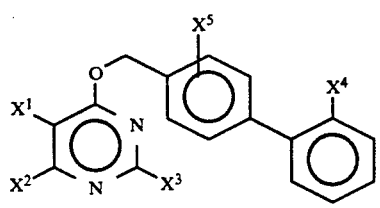

wherein:
$X^1$ is H, lower alkyl, phenyl, or naphthyl
$X^2$ is H, lower alkyl, phenyl, naphthyl, perfluoroalkyl or halogen,
or
$X^1$ and $X^2$ together are —(CH$_2$)$_n$— where n is 3–6;
$X^3$ is H, lower alkyl, perfluoroalkyl, perchloroalkyl or halogen,
$X^4$ is 5-tetrazolyl, carboxy or cyano;
$X^5$ is H, lower alkoxy or halogen;
or a pharmaceutically acceptable salt thereof.

2. A compound according to claim 1 wherein:
$X^1$ is H, methyl, propyl, isopropyl, tert-butyl, phenyl or naphthyl,
$X^2$ is H, methyl, ethyl, propyl, isopropyl, tert-butyl, phenyl, naphthyl, trifluoromethyl, perfluoroethyl, chlorine, bromine or fluorine;
or
$X^1$ and $X^2$ together are —(CH$_2$)$_3$— or —(CH$_2$)$_4$—;
$X^3$ is trifluoromethyl or methyl;
$X^4$ is 5-tetrazolyl,
and
$X^5$ is H, methoxy, fluorine, chlorine, or bromine.

3. A compound according to claim 1 which is 6-ethyl-5-propyl-4-[[(2'-1H-tetrazolyl-5-yl)biphenyl-4-yl]methoxy]-2-trifluoromethylpyrimidine or a pharmaceutically acceptable salt thereof.

4. A compound according to claim 1 which is 4-[[2'-(1H-tetrazol-5-yl)biphenyl-4-yl]methoxy]-2-trifluoromethyl-5,6,7,8-tetrahydroquinazoline or a pharmaceutically acceptable salt thereof.

5. A compound according to claim 1 which is 2,5-dimethyl-4-[[2'-(1H-tetrazol-5-yl)biphenyl-4-yl]methoxy]-6-trifluoromethylpyrimidine or a pharmaceutically acceptable salt thereof.

6. A method of treating hypertension which comprises administering to a warmblooded animal in need thereof a therapeutically effective amount of a compound having the formula:

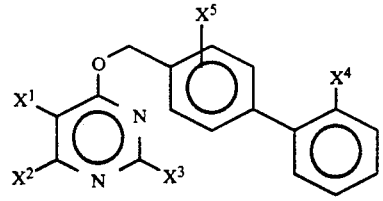

wherein:
$X^1$ is H, lower alkyl, phenyl or naphthyl
$X^2$ is H, lower alkyl, phenyl, naphthyl, perfluoroalkyl or halogen,
or
$X^1$ and $X^2$ together are —(CH$_2$)$_n$— where n is 3–6;
$X^3$ is H, lower alkyl, perfluoroalkyl, perchloroalkyl or halogen,
$X^4$ is 5-tetrazolyl, carboxy or cyano;
$X^5$ is H, lower alkoxy or halogen;
or a pharmaceutically acceptable salt thereof.

7. A method of treating hypertension according to claim 6 wherein:
$X^1$ is H, methyl, propyl, isopropyl, tert-butyl, phenyl or naphthyl;
$X^2$ is H, methyl, ethyl, propyl, isopropyl, tert-butyl, phenyl, naphthyl, trifluoromethyl, perfluoroethyl, chlorine, bromine or fluorine;
or
$X^1$ and $X^2$ together are —(CH$_2$)$_3$— or —(CH$_2$)$_4$—;
$X^3$ is trifluoromethyl or methyl;
$X^4$ is 5-tetrazolyl, and X[5] is H, methoxy, fluorine, chlorine, or bromine.

8. A method according to claim 6 wherein the compound used is 6-ethyl-5-propyl-4-[[2'-(1H-tetrazolyl-5-yl)biphenyl-4-yl]methoxy]-2-trifluoromethylpyrimidine or a pharmaceutically acceptable salt thereof.

9. A method according to claim 6 wherein the compound used is 4-[[2'-(1H-tetrazol-5-yl)biphenyl-4-yl]methoxy]-2-trifluoromethyl-5,6,7,8-tetrahydroquinazoline or a pharmaceutically acceptable salt thereof.

10. A method according to claim 6 wherein the compound used is 2,5-dimethyl-4-[[2'-(1H-tetrazol-5-yl)biphenyl-4-yl]methoxy]-6-trifluoromethylpyrimidine or a pharmaceutically acceptable salt thereof.

11. A pharmaceutical composition for treating hypertension which comprises a pharmaceutical carrier and a therapeutically effective amount of a compound having the formula:

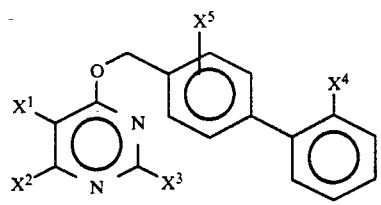

wherein:
  X[1] is H, lower alkyl, phenyl or naphthyl
  X[2] is H, lower alkyl, phenyl, naphthyl, perfluoroalkyl or halogen,
or
  X[1] and X[2] together are —(CH$_2$)$_n$— where n is 3–6;
  X[3] is H, lower alkyl, perfluoroalkyl, perchloroalkyl or halogen,
  X[4] is 5-tetrazolyl, carboxy or cyano;
  X[5] is H, lower alkoxy or halogen;
or a pharmaceutically acceptable salt thereof.

* * * * *